(12) United States Patent
Terry et al.

(10) Patent No.: US 6,576,816 B2
(45) Date of Patent: Jun. 10, 2003

(54) HEAVY METAL PHYTOREMEDIATION

(75) Inventors: Norman Terry, Berkeley, CA (US); Elizabeth Pilon-Smits, Fort Collins, CO (US); Yong Liang Zhu, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 138 days.

(21) Appl. No.: 09/933,549

(22) Filed: Aug. 20, 2001

(65) Prior Publication Data

US 2002/0016983 A1 Feb. 7, 2002

Related U.S. Application Data

(63) Continuation of application No. 09/365,349, filed on Jul. 30, 1999.

(51) Int. Cl.[7] ............... C12N 15/09; C12N 15/31; C12N 15/82; A01H 5/00
(52) U.S. Cl. ............... 800/306; 800/278; 800/288; 800/298; 435/69.1; 435/468; 435/419
(58) Field of Search ................. 800/278, 306, 800/288, 298; 435/69.1, 468, 419

(56) References Cited

U.S. PATENT DOCUMENTS

| | | | |
|---|---|---|---|
| 5,364,451 A | | 11/1994 | Raskin et al. ............... 75/710 |
| 5,747,329 A | * | 5/1998 | Meister et al. ............... 435/183 |

OTHER PUBLICATIONS

FEBS Letter (1998), 427(1):129–133.*
EMBO Journal (1997), 16(11):3057–3065.*
Journal of Biological Chemistry (1996), 271(29):17485–17490.*
PNAS (1998), 95(12049:12054).*
FEBS Letters (1997), 404:216–220.*
Watanabe et al. Nucleic Acids Research, Nov. 1986 14:4393–40.
Arisi et al. Planta, 1997 203:362–72.
Chen et al. Plant Physiol. 1994 106:233–39.
Noctor et al. Journal of Experimental Botany, Apr. 1998 49(321):623–47.
Peter Goldsbrough, Metal Tolerance in Plants: The role of phytochelatins and Metallothioneins. Ann Arbor Press, 1999 221–28.
Zhu et al. Plant Physiol. 1999 119:73–79.

* cited by examiner

*Primary Examiner*—Amy J. Nelson
*Assistant Examiner*—Medina A. Ibrahim
(74) *Attorney, Agent, or Firm*—Richard Aron Osman

(57) ABSTRACT

The invention provides methods and compositions for heavy metal phytoremediation, including plants which are genetically engineered to overexpress glutamylcysteine synthetase (ECS) and thereby provide enhanced heavy metal accumulation. In various embodiments, the plants comprise a gene encoding ECS operably linked to a heterologous promoter, the plant is a member of the Brassicaceae family. In general, the methods comprise the steps of growing such plants in a medium such as soil or water comprising a heavy metal, under conditions wherein ECS is overexpressed, whereby the plant provides enhanced accumulation of the heavy metal, whereby the heavy metal content of the medium is decreased.

23 Claims, No Drawings

HEAVY METAL PHYTOREMEDIATION

CROSS-REFERENCE TO RELATED APPLICATION

This application is a continuation Appl. Ser. No. 09/365,349, filed Jul. 30, 1999.

INTRODUCTION

1. Field of the Invention

The field of the invention is enhanced heavy metal phytoremediation by genetically engineered plants.

2. Background of the Invention

Heavy metals and metalloids such as cadmium, lead and mercury are an increasing environmental problem worldwide. Green plants can be used to remove heavy metals by sequestrating, stabilizing or biochemically transforming them. This cost-effective and environment-friendly technology has been called phytoremediation (Salt et al., 1995, Biotechnology 13:468–474). Hyperaccumulators—heavy metal accumulating flora collected from metal-contaminated sites—offer one option for the phytoremediation of metal-contaminated sites. However, these hyperaccumulators tend to grow slowly and produce little biomass. An alternative approach is to genetically engineer fast-growing species to improve their metal tolerance and metal accumulating capacity.

Non-protein thiols (NPTs), which contain a high percentage of cysteine sulfhydryl residues in plants, play a pivotal role in heavy metal detoxification. Glutathione (γ-Glu-Cys-Gly, GSH) is one of the most important components of NPT metabolism. GSH is thought to play multiple roles in heavy metal detoxification: it protects cells from oxidative stress damage; glutathione is a substrate for glutathione S-transferases and enables neutralization of heavy metals (Marrs, 1996, Annu Rev Plant Physiol Plant Mol Biol 47:127–158); and GSH is the direct precursor of phytochelatins (PCs). Phytochelatins are heavy metal-binding peptides involved in heavy metal tolerance and sequestration (Steffens, 1990). They comprise a family of peptides with the general structure (γ-Glu-Cys)$_n$-Gly, where n=2 to 11 (Rauser, 1995, Plant Physiol. 109: 1141–49). Phytochelatins were shown to be induced by heavy metals such as cadmium (Cd) in all plants tested (Zenk, 1996, Gene 179:21–30), including Indian mustard (Speiser et al. 1992, Plant Physiol. 99:817–821). The roles of glutathione in heavy metal tolerance and phytochelatin synthesis were illustrated in Cd-sensitive mutants of *Arabidopsis thaliana*. For example, the Cd-sensitive cad2 mutant was defective in glutathione biosynthesis (Howden et al., 1995, Plant Physiol 107:1067–1073). Glutathione is synthesized from its constituent amino acids in two sequential, ATP-dependent enzymatic reactions, catalyzed by γ-glutamyl-cysteine synthetase (ECS) and glutathione synthetase (GS), respectively. Phytochelatin synthase subsequently catalyzes the elongation of the (γ-Glu-Cys)$_n$ by transferring a γ-Glu-Cys group to glutathione or to PCs (Zenk, 1996; Chen et al., 1997, Physiol Plant 101:165–172).

Overexpressing the *Escherichia coli* gshII gene, encoding glutathione synthetase, in Indian mustard gave rise to plants with increased Cd tolerance and Cd accumulation (Zhu et al. 1999, Plant Physiol 119:73–79). These Indian mustard GS plants showed increased levels of glutathione and phytochelatins relative to untransformed plants, but only in the presence of heavy metals, confirming a series of reports indicating that GS is rate limiting for glutathione synthesis only in the presence of heavy metals. For example, overexpression of the *E. coli* gshII gene, encoding GS, does not normally increase foliar glutathione levels in poplar, but under heavy metal stress the regulation of glutathione biosynthesis undergoes a significant change. Heavy metals activate the PC synthase enzyme and thus induce the biosynthesis of PCs, resulting in a depletion of cellular glutathione levels (Zenk, 1996). Consequently, the feed-back inhibition of ECS by glutathione is released. Furthermore, ECS expression may be enhanced by heavy metals. It was demonstrated that Cd enhances the transcription of the ECS gene (Hatcher et al. 1995). In contrast, Cd may deactivate GS, as GS activity has previously been shown to be inhibited by Cd while the same Cd treatment had no affect on ECS activity (Schneider and Bergmann, 1995). Exposure of maize roots to Cd, besides causing a decline in GSH, caused an accumulation of γ-Glu-Cys, possibly because the activity of GSH synthetase was reduced in vivo (Rauser et al., 1991, Plant Physiol 97:128–138). Therefore, under Cd stress, the GS enzyme becomes rate-limiting for the biosynthesis of glutathione and PCs, and thus over-expression of gshII can alleviate the depletion of glutathione and enhance PC synthesis.

Though in the presence of heavy metals GS is rate limiting, in the absence of heavy metals ECS is rate-limiting (Zhu et al., 1999). For example, overexpression in poplar of the *E. coli* gshI gene, encoding g-ECS, resulted in increased foliar glutathione levels (Arisi et al., 1997, Planta 203:362–372). In the presence of heavy metals, expression of tomato ECS restored some degree of heavy metal tolerance to the cad2 *Arabidopsis thaliana* mutant. However, over-expression of this gene did not increase the Cd tolerance of wild type *A. thaliana* plants (Goldsbrough, 1999, Metal tolerance in plants: the role of phytochelatins and metallothioneins. In N Terry, G S Banuelos, eds, Phytoremediation of Trace Elements. Ann Arbor Press, Ann Arbor, Mich.) and reportedly failed to increase Cd accumulation in poplars (Noctor et al., 1998, J Exp Bot 49:523–647, 640). Nevertheless, based on fortuitous discoveries in our laboratory, we sought to obtain fast-growing plants with superior heavy metal accumulation and tolerance for phytoremediation by overexpressing ECS. We have successfully developed transgenic plants that have an increased ability for heavy metal accumulation and tolerance. These ECS plants greatly enhance the efficiency of heavy metal phytoextraction from polluted soils and wastewater.

SUMMARY OF THE INVENTION

The invention provides methods and compositions for heavy metal phytoremediation. The subject compositions include plants which are genetically engineered to overexpress glutamylcysteine synthetase and thereby provide enhanced heavy metal accumulation. In particular embodiments, the plants comprise a gene encoding ECS operably linked to a heterologous promoter, the plant is a member of the Brassicaceae family, such as *Brassica juncea*, and/or the heavy metal is cadmium. In general, the subject methods comprise the steps of growing such plants in a medium such as soil or water comprising a heavy metal, under conditions wherein the ECS is overexpressed, whereby the plant provides enhanced accumulation of the heavy metal, whereby the heavy metal content of the medium is decreased.

DESCRIPTION OF PARTICULAR EMBODIMENTS OF THE INVENTION

The following descriptions of particular embodiments and examples are offered by way of illustration and not by way of limitation. Unless contraindicated or noted otherwise, in these descriptions and throughout this specification, the terms "a" and "an" mean one or more, the term "or" means and/or and polynucleotide sequences are understood to encompass opposite strands as well as alternative backbones described herein.

The subject compositions include plants which are genetically engineered to overexpress ECS and thereby provide enhanced heavy metal accumulation. A wide variety of plants may be used, as urged by the particular heavy metal, medium, site geology, topology, weather, etc. Additional factors for selection include large biomass production, relatively high trace element accumulation capacity, and ease of genetic engineerability (Zhu et al., 1999). Suitable plants are readily screened for requisite engineerability and expression from examplars of candidate plant varieties by those skilled in the art of plant genetic engineering, as exemplified below. Suitable plants source materials include commercially available varieties of Acanthaceae, Aceraceae, Acoraceae, Adiantaceae, Agavaceae, Aizoaceae, Alismataceae, Alliaceae, Aloeaceae, Alstroemeriaceae, Amaranthaceae, Amaryllidaceae, Anacardiaceae, Anemiaceae, Angiopteridaceae, Annonaceae, Apocynaceae, Aponogetonaceae, Aquifoliaceae, Araceae, Araliaceae, Araucariaceae, Arecaceae, Aristolochiaceae, Asparagaceae, Aspleniaceae, Asteliaceae, Asteraceae, Balsaminaceae, Basellaceae, Bataceae, Begoniaceae, Berberidaceae, Betulaceae, Bignoniaceae, Bixaceae, Blechnaceae, Bombacaceae, Boraginaceae, Brassicaceae: *Alliaria petiolata, Arabidopsis thaliana, Arabis petiolaris, Arabis pumila,* Arabis sp., *Berteroa incana, Biscutella laevigata, Brassicajunceae, Brassica napus, Brassica napus* var. *napus, Brassica nigra, Brassica oleracea, Brassica oleracea* var. *gongylo, Capsella bursa-pastoris, Cardamine pratensis, Cochlearia officinalis, Dentaria laciniata, Descurainia pinnata, Draba asprella, Draba verna, Draba, Erysimum asperum, Erysimum asperum, Erysimum capitatum, Lepidiumflavum, Lepidium virginicum, Lesquerella argyraea, Lesquerella densiflora, Lesquerella rubicundula,* Lesquerella sp., *Lobularia maritima, Lunaria annua, Lunaria rediviva, Neobeckia aquatica, Nerisyrenia camporum, Physaria chambersii, Raphanus sativus, Sinapis alba, Stanleya pinnata, Streptanthus cordatus, Thlaspi arvense, Thlaspi rotundifolium,* Bromeliaceae, Buddlejaceae, Burseraceae, Buxaceae, Cabombaceae, Cactaceae, Caesalpiniaceae, Callitrichaceae, Calochortaceae, Calyceraceae, Campanulaceae, Cannabaceae, Cannaceae, Capparaceae, Caprifoliaceae, Caricaceae, Caryophyllaceae, Casuarinaceae, Celastraceae, Chenopodiaceae, Cistaceae, Clusiaceae, Cneoraceae, Cochlospermaceae, Combretaceae, Commelinaceae, Convallariaceae, Convolvulaceae, Comaceae, Corylaceae, Crassulaceae, Crossosomataceae, Cucurbitaceae, Cunoniaceae, Cupressaceae, Cuscutaceae, Cyatheaceae, Cycadaceae, Cyperaceae, Cyrillaceae, Dennstaedtiaceae, Dicksoniaceae, Didiereaceae, Dilleniaceae, Dioscoreaceae, Dipsacaceae, Dipterocarpaceae, Droseraceae, Dryopteridaceae, Ebenaceae, Ehretiaceae, Elaeagnaceae, Elaeocarpaceae, Elatinaceae, Empetraceae, Epacridaceae, Ephedraceae, Equisetaceae, Ericaceae, Eriocaulaceae, Erythroxylaceae, Escalloniaceae, Euphorbiaceae, Eupomatiaceae, Fabaceae, Fagaceae, Flacourtiaceae, Fouquieriaceae, Frankeniaceae, Fumariaceae, Gentianaceae, Geraniaceae, Gesneriaceae, Ginkgoaceae, Globulariaceae, Goodeniaceae, Grossulariaceae, Gunneraceae, Haemodoraceae, Haloragaceae, Hamamelidaceae, Heliconiaceae, Hippocastanaceae, Hyacinthaceae, Hydrangeaceae, Hydrophyllaceae, Hypericaceae, Iridaceae, Isoetaceae, Juglandaceae, Juncaceae, Koeberliniaceae, Krameriaceae, Lamiaceae, Lauraceae, Lecythidaceae, Lemnaceae, Lentibulariaceae, Liliaceae, Limnanthaceae, Limnocharitaceae, Linaceae, Loasaceae, Lobeliaceae, Loganiaceae, Lomandraceae, Lomariopsidaceae, Loranthaceae, Lycopodiaceae, Lythraceae, Magnoliaceae, Malpighiaceae, Malvaceae, Marantaceae, Marcgraviaceae, Marsileaceae, Martyniaceae, Mayacaceae, Melanthiaceae, Melastomataceae, Meliaceae, Melianthaceae, Menispermaceae, Menyanthaceae, Mimosaceae, Monimiaceae, Monotropaceae, Moraceae, Musaceae, Myoporaceae, Myricaceae, Myristicaceae, Myrsinaceae, Myrtaceae, Nelumbonaceae, Nyctaginaceae, Nymphaeaceae, Nyssaceae, Ochnaceae, Oenotheraceae, Oleaceae, Oliniaceae, Onagraceae, Ophioglossaceae, Orchidaceae, Orobanchaceae, Osmundaceae, Oxalidaceae, Paeoniaceae, Pandanaceae, Papaveraceae, Passifloraceae, Pedaliaceae, Philydraceae, Phormiaceae, Phytolaccaceae, Pinaceae, Piperaceae, Pittosporaceae, plantaginaceae, Platanaceae, Plumbaginaceae, Poaceae, Podocarpaceae, Podophyllaceae, Polemoniaceae, Polygalaceae, Polygonaceae, Polypodiaceae, Pontederiaceae, Portulacaceae, Primulaceae, Proteaceae, Pteridaceae, Punicaceae, Pyrolaceae, Rafflesiaceae, Ranunculaceae, Resedaceae, Restionaceae, Rhamnaceae, Rosaceae, Rubiaceae, Ruscaceae, Rutaceae, Salicaceae, Salviniaceae, Santalaceae, Sapindaceae, Sapotaceae, Sarraceniaceae, Saururaceae, Saxifragaceae, Scrophulariaceae, Selaginellaceae, Simaroubaceae, Smilacaceae, Solanaceae, Sparganiaceae, Sterculiaceae, Strelitziaceae, Styracaceae, Taccaceae, Tamaricaceae, Taxaceae, Taxodiaceae, Theaceae, Thelypteridaceae, Thymelaeaceae, Tiliaceae, Trapaceae, Tremandraceae, Trilliaceae, Trochodendraceae, Tropaeolaceae, Tumeraceae, Typhaceae, Ulmaceae, Urticaceae, Valerianaceae, Verbenaceae, Veronicaceae, Violaceae, Viscaceae, Vitaceae, Welwitschiaceae, Winteraceae, Xanthorrhoeaceae, Xerophyllaceae, Xyridaceae, Zamiaceae, Zingiberaceae, and Zygophyllaceae. Preferred plant species include members of the Salicaceae family, such as *Populus angustifolia;* the Solanaceae family, such as *Nicotiana tabacum;* the Caryophyllaceae family, such as *Silene cucubalis;* and the Brassicaceae family, such as *Brassica juncea.*

In particular embodiments, the plants comprise a gene encoding ECS operably linked to a heterologous promoter. A wide variety of ECS genes are known in the art or readily isolated from target cells. The precise nature of the ECS recombinant expression construct is not essential so long as the requisite expression and associated heavy metal accumulation increase is effected. For example, in a particular embodiment, the *E. coli* gshI gene, fused to a pea chloroplast transit sequence and driven by the double-enhanced 35S CaMV promoter. Other suitable promoter examples include the nos promoter, 35S-35S, and 35S with the AMV leader sequence. The ECS construct may also comprise additional elements, such as a selectable marker. For example, in a particular embodiment, the construct contains the nptII gene, which confers kanamycin resistance.

The subject plants and methods are amenable to accumulating a wide variety of heavy metals, wherein the applicability to any target metal is readily determined empirically, as in the methods described herein. In particular embodiments, the metal is selected from cadmium, lead, mercury, beryllium, barium, copper, manganese, nickel, tin, vanadium, zinc, chromium, iron, molybdenum, tungsten, cobalt, gold, uranium and silver. In other embodiments, the metal encompasses semi-metallic elements such as boron, arsenic, selenium, polonium and tellurium; preferably metals of common site contamination and with relatively high human or environmental toxicity, such as cadmium, mercury and chromium.

In general, the subject methods comprise the steps of: (a) identifying a medium such as soil or water as containing an excessive amount of a heavy metal; and (b) growing the subject plants in the medium, under conditions wherein ECS is overexpressed, whereby the plant provides enhanced accumulation of the heavy metal, whereby the heavy metal content of the medium is decreased. The decrease may be measured directly or indirectly, as accumulation in the plants. In particular embodiments, the decrease is measured as enhanced accumulation of at least 50%, preferably at least 80%, more preferably at least 200% greater than an otherwise comparable unengineered plant.

Table 2 shows exemplary transformed plant species demonstrating enhanced heavy metal accumulation over wild-type counterparts, as described below.

Table 2. Exemplary plant species demonstrating enhanced heavy metal accumulation in wild-type plants (wt) and the corresponding plant overexpressing recombinant glutamylcysteine synthetase (r); experimental material and methods substantially as described below.

TABLE 2

Exemplary plant species demonstrating enhanced heavy metal accumulation in wild-type plants (wt) and the corresponding plant overexpressing recombinant glutamylcysteine synthetase (r); experimental material and methods substantially as described below.

| Plant Species | ECS gene | Promoter | Element | Medium | wt | r |
|---|---|---|---|---|---|---|
| Brassica juncea | E. coli | 35S CaMV | Cd | hydroponic | +/− | +++ |
| Brassica juncea | E. coli | 35S CaMV | Mo | hydroponic | +/− | +++ |
| Brassica juncea | E. coli | 35S CaMV | W | hydroponic | +/− | +++ |
| Brassica juncea | E. coli | 35S CaMV | Hg | hydroponic | +/− | +++ |
| Brassica juncea | E. coli | 35S CaMV | U | hydroponic | +/− | +++ |
| Brassica juncea | E. coli | 35S CaMV | Se | hydroponic | +/− | +++ |
| Brassica juncea | S. cerevisiae | 35S CaMV | Cd | hydroponic | +/− | +++ |
| Brassica juncea | B. juncea | 35S CaMV | Cd | hydroponic | +/− | +++ |
| Brassica juncea | human | 35S CaMV | Cd | hydroponic | +/− | +++ |
| Brassica juncea | E. coli | nos | Cd | hydroponic | +/− | +++ |
| Brassica juncea | E. coli | 35S-35S | Cd | hydroponic | +/− | +++ |
| Brassica juncea | E. coli | 35S-AMV | Cd | hydroponic | +/− | +++ |
| Populus angustifolia | E. coli | 35S CaMV | Cd | hydroponic | +/− | +++ |
| Populus angustifolia | E. coli | 35S CaMV | Mo | hydroponic | +/− | +++ |
| Populus angustifolia | E. coli | 35S CaMV | W | hydroponic | +/− | +++ |
| Populus angustifolia | E. coli | 35S CaMV | Hg | hydroponic | +/− | +++ |
| Populus angustifolia | E. coli | 35S CaMV | U | hydroponic | +/− | +++ |
| Populus angustifolia | E. coli | 35S CaMV | Se | hydroponic | +/− | +++ |
| Nicotina tabacum | E. coli | 35S AMV | Cd | hydroponic | +/− | +++ |
| Silene cucubalis | E. coli | 35S CaMV | Cd | hydroponic | +/− | +++ |
| Brassica juncea | E. coli | 35S CaMV | Cd | loamy soil | +/− | +++ |
| Populus angustifolia | E. coli | 35S CaMV | Cd | loamy soil | +/− | +++ |
| Nicotiana tabacum | E. coli | 35S CaMV | Cd | loamy soil | +/− | +++ |
| Silene cucubalis | E. coli | 35S CaMV | Cd | loamy soil | +/− | +++ |
| Brassica juncea | E. coli | 35S CaMV | Cd | sandy soil | +/− | +++ |
| Populus angustifolia | E. coli | 35S CaMV | Cd | sandy soil | +/− | +++ |
| Nicotiana tabacum | E. coli | 35S CaMV | Cd | sandy soil | +/− | +++ |
| Silene cucubalis | E. coli | 35S CaMV | Cd | sandy soil | +/− | +++ |
| Brassica juncea | E. coli | 35S CaMV | Cd | clay soil | +/− | +++ |
| Populus angustifolia | E. coli | 35S CaMV | Cd | clay soil | +/− | +++ |
| Nicotiana tabacum | E. coli | 35S CaMV | Cd | clay soil | +/− | +++ |
| Silene cucubalis | E. coli | 35S CaMV | Cd | clay soil | +/− | +++ |

EXPERIMENTAL PROTOCOLS AND RESULTS FOR EXEMPLARY EMBODIMENT

Plant transformation and characterization. Indian mustard seeds (*Brassica juncea*, accession no. 173874), were obtained from the North Central Regional Plant Introduction Station, Ames, Iowa. Hypocotyl segments from 3 d old axenically grown Indian mustard seedlings were transformed as described by Pilon-Smits et al. (1999, Plant Physiol 119:123–132). The ECS gene construct used was described earlier by Arisi et al. (1997). It contains the *E. coli* gshI gene, fused to a pea chloroplast transit sequence and driven by the double-enhanced 35S CaMV promoter. The construct also contains the nptII gene, which confers kanamycin resistance.

PCR was used to identify ECS transgenic lines among the kanamycin-resistant lines obtained: the forward primer was directed against the 35S promoter and the reverse primer was directed at the gshI gene. Total RNA was isolated from 7 d old seedling shoots using the RNeasy Plant Mini Kit (Qiagen). Northern blot hybridization was carried out as described by Krumlauf (1994, Mol Biotechnol 2:227–242), using a gshI DNA probe that was generated by PCR using the primers described above. The PCR product was purified from gel and labeled with 32P-dCTP by random priming (Feinberg and Vogelstein, 1983). The RNA blots were stained with methylene blue to check for equal loading and transfer (Herrin and Schmidt, 1988).

For Western blotting, 7 d old seedlings (shoots and roots separately) were ground in liquid nitrogen and extracted in 50 mM potassium phosphate buffer, pH 8, added at 1 ml g-1 FW. After measurement of total protein concentration (Bradford, 1976, Anal Biochem 72:248–254), 10 μg of protein from each sample was separated by SDS-PAGE and blotted onto a zeta probe membrane (Biorad) by electroblotting. We used the Biorad Immun-lite kit for the immunodetection of separated proteins, and rabbit serum raised against purified *E. coli* glutamylcysteine synthetase as first antibody (Arisi et al., 1997).

Plant growth and tolerance experiments. Seedling experiments: T2 seeds from transgenic lines ECS2, ECS4 and wild type Indian mustard were sterilized by rinsing them in 95% ethanol for 30 seconds, then in 1% hypochlorite solution for 30 minutes, and subsequently in sterile deionized water for five times, 10 minutes each time, all on a rocking platform. Fifty sterilized seeds were sown in a grid pattern in Magenta boxes (Sigma) on half-strength MS medium containing 10 g $L^{-1}$ sucrose, 5 g $L^{-1}$ phytagar (Sigma), and different concentrations of $CdSO_4$ (0, 0.15, 0.20, or 0.25 mM). After 7 days at 25° C. under continuous light, the individual seedlings were harvested, washed, weighed and the length of the longest root was measured.

Mature plant experiments: Seeds of ECS2, ECS4 and wild type Indian mustard were sterilized and sown in Magenta boxes as described above. After 5 days on agar the seedlings were transferred to 4" pots containing coarse sand. The pots were maintained in a greenhouse with controlled temperature (24° C.) and a short-day (9 h) photoperiod (to prevent them from flowering). The plants were watered twice a day, once with tap water and once with 0.5 strength Hoagland's solution. After 6 weeks of growth under these conditions, the plants were gently washed in water to remove the sand adhering to the roots and transferred to a nutrient film technique (NFT) setup (Zayed, 1987, Influence of sodium chloride on ion uptake and yield of tomatoes and lettuce grown by hydroponics. Ph.D. Thesis. Wye College, University of London). Briefly, the plants were placed in channels and quarter-strength Hoagland's nutrient solution (Hoagland and Arnon, 1938, CA Agricultural Experiment Station Circulation 347:1–39) amended with 0.05, 0.075 and 0.1 mM Cd (as $CdSO_4$) was circulated along the plant roots. The NFT setup was maintained under the same greenhouse conditions as described earlier. Plants were harvested after 14 d and thoroughly washed under running deionized water to remove any trace elements adhering to the tissue. Total fresh weights of the plants were measured before and after the experiment to determine the effect of different concentrations of Cd on growth. Shoot and root tissues were separated and dried at 70° C. for 3 days. The dried tissues were weighed and then ground in a Wiley mill.

Glutathione and non-protein thiol analysis. Non-protein thiols (NPTs) and GSH were measured from the seedlings used for the Cd experiment. For NPTs, extracts were prepared according to the method described by Galli et al. (1996, Planta 198:139–143), by adding 300 μl of a solution containing 1M NaOH and 1 mg $L^{-1}$ $NaBH_4$ to 100 mg of homogenized plant sample. The homogenate was centrifuged for 3 min at 13,000×g at 4° C. 300 μL of the supernatant was acidified by adding 50 μL of 37% HCl. NPT contents were measured spectrophotometrically by adding 20 μL of this solution to 1 mL of of 5,5'-dithiobis(2-nitrobenzoic acid) (Ellman's reagent, Ellman 1959, Arch Biochem Biophys 82:70–77), followed by the measurement of the absorption at 412 nm. Total glutathione was measured according to Hermsen et al. (1997, Plant Physiol Biochem 35:491–496).

Elemental analysis. Elemental analysis was carried out after acid digestion of dried and ground tissue samples as described by Zarcinas et al. (1987, Commun Soil Sci Plant Anal 18:131–146). The concentrations of trace elements in the acid digest were measured by inductively-coupled plasma emission spectroscopy (ICP-AES, Fassel, 1978, Science 202:183–191). Standards (NIST) and blanks were run with all samples for quality control. Plants that had not been supplied with trace elements were also analyzed for trace element concentrations, as a negative control.

Statistical analyses were performed using the JMP IN statistical package (SAS Institute).

Production and characterization of transgenic ECS plants. Five kanamycin-resistant Indian mustard lines were obtained after transformation with the gshI construct, designated ECS1, ECS2, ECS3, ECS4 and ECS6. All five plant lines showed a PCR product when PCR was performed using primers directed against the 35S promoter and the gshI gene (not shown). Progeny of lines ECS2 and ECS4 showed a kanamycin resistance ratio of 3:1 (100 mg.$L^{-1}$ in half-strength MS medium) after self-fertilization of the first generation, indicating a single insert of the gshI gene; lines ECS1, ECS3 and ECS6 showed kanamycin resistance ratios less than 3:1. Homozygous T2 lines from individual T1 plants of lines ECS2 and ECS4 were used for subsequent experiments. These transgenic T1 and T2 plants did not show any phenotypic differences compared to the untransformed Indian mustard plants.

Antiserum raised against *E. coli* glutamylcysteine synthetase was used to analyze the ECS expression levels in the transgenic lines at the protein level. On Western blots, shoot tissues from ECS2 and ECS4 lines were both shown to contain a protein with the same molecular weight as the *E. coli* glutamylcysteine synthetase (64 kD), which reacted with the antiserum; no band was detected in wild type extract. The expression level of the *E. coli* ECS protein was a little higher in ECS4 than in ECS2. When gshI DNA was used as a probe for a Northern blot containing total RNA isolated from T2 seedlings of ECS2 and ECS4, both transgenic lines showed a band of 1.85 kb, a size corresponding with the *E. coli* gshI transcript.

ECS plants show improved Cd accumulation and tolerance. Two experiments were conducted to test Cd tolerance, either using seedlings or mature plants. In the seedling experiments, seeds of lines ECS2 and ECS4 and seeds from wild type Indian mustard were sown on agar medium containing 0, 0.15, 0.20, or 0.25 mM of $CdSO_4$, and root length was measured after 6 days. Root length is considered to be a reliable parameter for trace element tolerance (Murphy and Taiz, 1995, Plant Physiol 108:29–38). At all three Cd concentrations, the ECS seedlings had significantly longer roots than wild type seedlings. For example, at 0.20 mM Cd, the roots of ECS4 seedlings were more than two-fold longer ($P<0.001$) than those of wild type seedlings. The shoots of the transgenic seedlings were also taller than shoots of wild type seedlings, under Cd treatment. Under control conditions there were no significant differences in root or shoot length between the ECS seedlings and the wild type seedlings.

The Cd tolerance experiments with mature plants were performed with plants from transgenic lines ECS2, ECS4, and wild type. After 12 d of growth on 0, 0.05, 0.075 or 0.10 mM $CdSO_4$, the ECS plants showed superior Cd tolerance compared to wild type: their growth was less inhibited by Cd than the growth of wild type plants ($P<0.05$). For instance, in nutrient solution amended with 0.05 mM Cd, the relative growth of ECS2 plants was 44% of that of untreated ECS2 controls, while the relative growth of wild type plants was 30%. The total Cd concentration in plant roots and shoots was determined for the mature plant experiments. Both ECS2 and ECS4 plants showed higher Cd concentrations in their shoots than wild type plants. For example, when grown at 0.05 mM external Cd the shoot Cd concentrations in ECS4 plants were 90% higher than in wild type plants (P<0.01). The Cd concentration in roots of ECS2 and ECS4 plants was also somewhat higher than in wild type plants, but this difference was not significant.

ECS plants contain higher levels of GSH and NPTs. To investigate the effect of ECS overexpression on the production of heavy metal binding compounds, the levels of glutathione and total NPTs (including cysteine, g-Glu-Cys, GSH and PCs, etc.) were determined in shoot samples collected from ECS2, ECS4 and wild type seedlings used in the seedling experiment described above, treated with 0.15, 0.20 or 0.25 mM Cd. The glutathione levels were 1.5 to 2.5-fold higher in both ECS lines compared to wild type (P<0.05). This difference was true for both Cd-treated and non-treated seedlings. Under control conditions, the GSH level was 141 nmol $g^{-1}$ FW in wild type while it was 363 nmol $g^{-1}$ FW in ECS4. At 0.1 mM Cd, the GSH level in ECS4 (140 nmol $g^{-1}$ FW) was also double that in wild type (67 nmol $g^{-1}$ FW). The GSH levels in Cd-treated wild type and ECS seedlings were significantly lower than in untreated seedlings.

Cadmium treatment increased NPT levels 4 to 6-fold in both wild type and ECS plants. ECS2 and ECS4 plants had slightly higher levels of total NPTs than wild type under control conditions (1.36, 1.80 and 1.16 mM $g^{-1}$ FW respectively), but this difference was not significant. In contrast, the thiol levels in Cd-treated ECS seedlings were significantly higher (approximately 1.5-fold) than in wild type seedlings.

Effects of ECS overexpression on mineral nutrient levels. To investigate the effect of Cd on the mineral nutrient levels of other elements, the contents of B, Ca, Cu, Fe, K, Mg, Mn, Mo, P, S, and Zn were determined in shoots and roots of mature ECS4 and wild type plants, treated with 0 or 0.1 mM Cd. When plants were grown in the absence of Cd there were no significant differences between ECS and wild type plants with respect to tissue concentrations of any of these elements except for Cu and Zn: ECS4 shoots had higher levels of Cu (P=0.02) and Zn (P=0.06) than wild type shoots. When grown in the presence of 0.1 mM Cd, the root concentrations of all elements tested including Zn and Cu did not show any significant difference between ECS4 and wild type plants. In the group of Cd-treated plants, ECS plants had significantly higher levels of Cu in their roots than wild type plants, but there was no difference in Zn concentration. Cadmium treatment had significant effects on the nutrient levels of some elements in the plants. In wild type plants, the levels of Ca, Fe, Mn, and P were significantly lower under 0.1 mM Cd treatment than under non-Cd conditions (levels of B, Mg, K and Mo were not affected by Cd). Interestingly, the levels of Ca, Fe, Mn and P were all significantly higher in Cd-treated ECS4 plants than in Cd-treated wild type plants. Interestingly, the tissue Ca concentration was significantly enhanced by Cd in ECS4 plants, from 27,759 to 36,504 mg $kg^{-1}$ DW, while in wild type plants they were reduced from 32,785 to 20,247 mg $kg^{-1}$ DW. The S levels were also higher in Cd-treated ECS4 plants (1956 mg $kg^{-1}$ DW) than in Cd-treated wild type plants (718.7 mg $kg^{-1}$ DW) (P<0.01).

All publications and patent applications cited in this specification and all references cited therein are herein incorporated by reference as if each individual publication or patent application or reference were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A Brassica plant which is genetically engineered to overexpress glutamylcysteine synthetase and thereby provides enhanced heavy metal accumulation as compared with a corresponding wild type plant.

2. A plant according to claim 1 comprising a gene encoding the glutamylcysteine synthetase operably linked to a heterologous promoter.

3. A plant according to claim 1 which is a *Brassica juncea*.

4. A plant according to claim 1 wherein the heavy metal is selected from the group consisting of chromium, molybdenum and tungsten.

5. A plant according to claim 1 wherein the heavy metal is selected from the group consisting of cadmium and mercury.

6. A plant according to claim 1 wherein the heavy metal is uranium.

7. A plant according to claim 1, wherein the enhanced accumulation is at least 50% greater than an otherwise comparable untransformed plant.

8. A plant according to claim 1, wherein the plant comprises a gene encoding the glutamylcysteine synthetase operably linked to a heterologous promoter, the plant is a *Brassica juncea*, the heavy metal is selected from the group consisting of chromium, molybdenum and tungsten and the enhanced accumulation is at least 50% greater than an otherwise comparable untransformed plant.

9. A plant according to claim 1, wherein the plant comprises a gene encoding the glutamylcysteine synthetase operably linked to a heterologous promoter, the plant is a *Brassica juncea*, the heavy metal is selected from the group consisting of cadmium and mercury and the enhanced accumulation is at least 50% greater than an otherwise comparable untransformed plant.

10. A plant according to claim 1, wherein the plant comprises a gene encoding the glutamylcysteine synthetase operably linked to a heterologous promoter, the plant is a *Brassica juncea*, the heavy metal is selected from the group consisting of tellurium and polonium and the enhanced accumulation is at least 50% greater than an otherwise comparable untransformed plant.

11. A plant according to claim 1, wherein the plant comprises a gene encoding the glutamylcysteine synthetase operably linked to a heterologous promoter, the plant is a *Brassica juncea*, the heavy metal is uranium and the enhanced accumulation is at least 50% greater than an otherwise comparable untransformed plant.

12. A method for decreasing heavy metal content of a medium, comprising the steps of: (a) identifying a medium as containing an excessive amount of a heavy metal; and (b) growing a plant according to claim 1 in the medium, under conditions wherein the glutamylcysteine synthetase is overexpressed, whereby the plant provides enhanced accumulation of the heavy metal, whereby the heavy metal content of the medium is decreased.

13. A method for decreasing heavy metal content of a medium, comprising the steps of: (a) identifying a medium as containing an excessive amount of a heavy metal; and (b) growing a plant according to claim 6 in the medium, under conditions wherein the glutamylcysteine synthetase is overexpressed, whereby the plant provides enhanced accumulation of the heavy metal, whereby the heavy metal content of the medium is decreased.

14. A method for decreasing heavy metal content of a medium, comprising the steps of: (a) identifying a medium as containing an excessive amount of a heavy metal; and (b) growing a plant according to claim 7 in the medium, under conditions wherein the glutamylcysteine synthetase is overexpressed, whereby the plant provides enhanced accumulation of the heavy metal, whereby the heavy metal content of the medium is decreased.

15. A method for decreasing heavy metal content of a medium, comprising the steps of: (a) identifying a medium as containing an excessive amount of a heavy metal; and (b) growing a plant according to claim 8 in the medium, under conditions wherein the glutamylcysteine synthetase is overexpressed, whereby the plant provides enhanced accumulation of the heavy metal, whereby the heavy metal content of the medium is decreased.

16. A method for decreasing heavy metal content of a medium, comprising the steps of: (a) identifying a medium as containing an excessive amount of a heavy metal; and (b) growing a plant according to claim 9 in the medium, under conditions wherein the glutamylcysteine synthetase is overexpressed, whereby the plant provides enhanced accumulation of the heavy metal, whereby the heavy metal content of the medium is decreased.

17. A method for decreasing heavy metal content of a medium, comprising the steps of: (a) identifying a medium as containing an excessive amount of a heavy metal; and (b) growing a plant according to claim 10 in the medium, under conditions wherein the glutamylcysteine synthetase is overexpressed, whereby the plant provides enhanced accumulation of the heavy metal, whereby the heavy metal content of the medium is decreased.

18. A method according to claim 12, wherein the medium is soil.

19. A plant according to claim 1 wherein the plant grows not significantly differently than a corresponding wild type plant under non-heavy metal conditions.

20. A plant according to claim 3 wherein the plant grows not significantly differently than a corresponding wild type plant under non-heavy metal conditions.

21. A method according to claim 12 wherein the plant grows not significantly differently than a corresponding wild type plant under non-heavy metal conditions.

22. A method according to claim 15 wherein the plant grows not significantly differently than a corresponding wild type plant under non-heavy metal conditions.

23. A method according to claim 16 wherein the plant grows not significantly differently than a corresponding wild type plant under non-heavy metal conditions.

* * * * *

UNITED STATES PATENT AND TRADEMARK OFFICE
CERTIFICATE OF CORRECTION

PATENT NO. : 6,576,816 B2
DATED : June 10, 2003
INVENTOR(S) : Terry et al.

It is certified that error appears in the above-identified patent and that said Letters Patent is hereby corrected as shown below:

Column 10,
Line 4, "is genetically engineered" should read -- comprises a recombinant glutamylcysteine synthetase expression construct --;
Line 8, "A" should read -- The --, and "comprising" should read -- wherein the expression construct comprises --;
Lines 11, 12, 15, 18 and 20, "A" should read -- The --;
Lines 23, 30, 37 and 44, "A" should read -- The --, and "plant" should read -- expression construct --;
Lines 53 and 61, "a" should read -- the --.

Column 11,
Lines 2, 10 and 18, "a" should read -- the --.

Column 12,
Line 1, "a" should read -- the --;
Lines 6, 8, 11, 14, 17 and 20, "A" should read -- The --.

Signed and Sealed this

Twenty-second Day of July, 2003

JAMES E. ROGAN
*Director of the United States Patent and Trademark Office*